(12) United States Patent
Guardiola et al.

(10) Patent No.: US 6,337,094 B1
(45) Date of Patent: Jan. 8, 2002

(54) AQUEOUS SOLUTION FOR THE PARENTERAL NUTRITION

(75) Inventors: Jaime Guardiola, Homburg; Martin Wolf, Melsungen, both of (DE)

(73) Assignee: B. Braun Melsungen (DE)

( * ) Notice: Subject to any disclaimer, the term of this patent is extended or adjusted under 35 U.S.C. 154(b) by 0 days.

(21) Appl. No.: 09/604,115

(22) Filed: Jun. 26, 2000

(30) Foreign Application Priority Data

Jun. 26, 1999 (EP) .............................. 99112319

(51) Int. Cl.⁷ ...................... A61K 33/42; A61K 31/415; A61K 31/40; A61K 31/195

(52) U.S. Cl. ...................... 424/602; 514/400; 514/419; 514/561; 514/565

(58) Field of Search .................... 424/602; 514/400, 514/419, 561, 565

(56) References Cited

U.S. PATENT DOCUMENTS 5,206,269 A  4/1993  Ludwig et al.

FOREIGN PATENT DOCUMENTS

| DE | 3916903 | 2/1991 |
| DE | 4316326 | 6/1994 |
| EP | 0671166 | 9/1995 |
| EP | 0705542 | 4/1996 |
| EP | 0712583 | 5/1996 |

*Primary Examiner*—Raymond Henley, III
(74) *Attorney, Agent, or Firm*—Brobeck, Phleger & Harrison, LLP

(57) ABSTRACT

The invention refers to an aqueous solution for the parenteral nutrition of mammals consisting of:

a) a pattern of amino acids calculated on the basis of 100 g/l of amino acids:

| | |
|---|---|
| Isoleucine | 4.0–5.5 g/l |
| Leucine | 8.0–10.0 g/l |
| Lysine | 6.0–8.0 g/l |
| Methionine | 4.0–6.0 g/l |
| Phenylalanine | 4.0–6.0 g/l |
| Threonine | 4.0–6.0 g/l |
| Tryptophane | 1.0–2.0 g/l |
| Valine | 6.0–8.0 g/l |
| Arginine | 10.0–12.0 g/l |
| Histidine | 1.5–3.5 g/l |
| Alanine | 9.0–12.0 g/l |
| Aminoacetic Acid (Glycine) | 11.0–16.0 g/l |
| Asparagine | 0–1.0 g/l |
| Aspartic Acid | 5.5–8.0 g/l |
| Acetylcysteine | 0–2.5 g/l |
| Glutamic Acid | 6.0–10.0 g/l |
| Ornithine | 0–1.0 g/l |
| Proline | 4.0–6.0 g/l |
| Serine | 1.0–3.0 g/l |
| Tyrosine* | 01.–0.5 g/l |
| *as Acetyltyrosine | 0–2.0 g/l |
| Taurine | 0–4.0 g/l | b) a pattern of electrolytes of:

| | |
|---|---|
| Sodium | 0–100.0 mmol/l |
| Potassium | 0–80.0 mmol/l |
| Magnesium | 0–8.0 mmol/l |
| Calcium | 0–8.0 mmol/l and/or |
| Zinc | 0–0.08 mmol/l |
| Phosphate | 0–20.0 mmol/l |
| Chloride | 0–120.0 mmol/l |
| Acetate | 0–120.0 mmol/l |
| Citric acid | 0–10.0 mmol/l |
| Malate | 0–80.0 mmol/l |
| Lactate | 0–10.0 mmol/l |
| Glycerophosphate | 0–30.0 mmol/l and/or |
| Gluconate | 0–120.0 mmol/l | and c) optionally a carbohydrate solution and/or a fat emulsion.

10 Claims, No Drawings

AQUEOUS SOLUTION FOR THE PARENTERAL NUTRITION

The invention refers to an aqueous solution for the parenteral nutrition of mammals.

EP 0 671 166 A2 discloses an infusion preparation for nutrient supply use. It comprises sugar, amino acids, electrolytes and fat emulsion. The examples disclose several patterns of amino acids.

In the same way DE 43 16 326 C1 discloses different patents of amino acids for the total parenteral nutrition by perivenous application.

Similar to that disclosure of DE 43 16 326 C1, DE 39 16 903 A1 discloses an aqueous composition of parenteral nutrition which is in particular defined by a specific amino acid pattern.

R. Zander, Infusionsther. Transfusionsmed. 1993;20:217–235 discloses a specific base concept for infusion solutions. In particular, the concepts of base excess (BE mmol/l and BE pot. mmol/l) should be introduced, in order to give an indication of potential alterations in the $HCO_{3-}$ pool after infusion and metabolism of infusion solutions. This also applies to blood derivatives, where transfusion acidosis as well as alkalosis may occur, and in hemodialysis and peritoneal dialysis where the occurrence of acidosis and alkalosis during therapy need to be reckoned with. The above mentioned patterns of amino acid solutions partially available in the market do not fulfill the requirements of the concept of a base excess.

Thus, it was the object of the invention to provide an aqueous solution for the parenteral nutrition of mammals fulfilling the requirements of said concept.

The solution of the above mentioned object is fulfilled in a first embodiment by an aqueous solution of the parenteral nutrition of mammals consisting of a) a pattern of amino acids calculated on the basis of 100 g/l of amino acids

| | |
|---|---|
| Isoleucine | 4.0–5.5 g/l |
| Leucine | 8.0–10.0 g/l |
| Lysine | 6.0–8.0 g/l |
| Methionine | 4.0–6.0 g/l |
| Phenylalanine | 4.0–6.0 g/l |
| Threonine | 4.0–6.0 g/l |
| Tryptophane | 1.0–2.0 g/l |
| Valine | 6.0–8.0 g/l |
| Arginine | 10.0–12.0 g/l |
| Histidine | 1.5–3.5 g/l |
| Alanine | 9.0–12.0 g/l |
| Aminoacetic Acid (Glycine) | 11.0–16.0 g/l |
| Asparagine | 0–1.0 g/l |
| Aspartic Acid | 5.5–8.0 g/l |
| Acetylcysteine | 0–2.5 g/l |
| Glutamic Acid | 6.0–10.0 g/l |
| Ornithine | 0–1.0 g/l |
| Proline | 4.0–6.0 g/l |
| Serine | 1.0–3.0 g/l |
| Tyrosine* | 01.–0.5 g/l |
| *as Acetyltyrosine | 0–2.0 g/l |
| Taurine | 0–4 g/l | b) a pattern of electrolytes of

| | |
|---|---|
| Sodium | 0–100.0 mmol/l |
| Potassium | 0–80.0 mmol/l |
| Magnesium | 0–8.0 mmol/l |
| Calcium | 0–8.0 mmol/l and/or |
| Zinc | 0–0.08 mmol/l |
| Phosphate | 0–20.0 mmol/l |
| Chloride | 0–120.0 mmol/l |
| Acetate | 0–120.0 mmol/l |
| Citric acid | 0–10.0 mmol/l |
| Malate | 0–80.0 mmol/l |
| Lactate | 0–10.0 mmol/l |
| Glycerophosphate | 0–30.0 mmol/l and/or |
| Gluconate | 0–120.0 mmol/l | c) optionally a carbohydrate solution (sugar) and/or fat emulsion.

Parenteral nutrition must supply the body with all the components necessary for growth and tissue generation. The amino acids play a prominent role since they are the basic components for protein synthesis. In order to ensure optimal utilization of the amino acids, the administration of an additional energy source is required. This can be fulfilled partly in the form of the optionally used carbohydrates. As glucose can be utilized directly, it is the carbohydrate of choice, but in the same way Xylitol can be utilized instead of or partially substituting glucose.

However, the prior art of course discloses the use of other carbohydrates.

Electrolytes are administered for the maintenance of metabolic and physiologic function. They ensure an adequate parenteral nutritional supply with the aqueous solution.

Following intravenous infusion the constituents of the solution according to the present invention are immediately available for metabolism due to the specific pattern of the ingredients. Therefore, no further investigations on the bioavailability are necessary. A portion of the amino acids is used for proteins synthesis, the rest being broken as following: The amino groups are separated by transamination and the carbon moiety is either oxidized to $CO_2$ in the citrate cycle or utilized in the liver as a substrate for a gluconeogenesis. The amino groups resulting for protein breakdown in muscle tissue are transported to the liver, where urea is synthesized. The ingredients of the aqueous solution according to the present invention are naturally occurring substances or metabolic intermediates and their concentration after appropriate infusion is similar to physiological levels.

The overall content of the amino acids may be varied according to the necessity of the patient to be administered therewith. Thus, the overall content of the amino acids in aqueous solutions according to the present invention may vary between 20 to 180 g/l. Nevertheless, it is to be ensured that the scope of pattern as mentioned above is not left. Accordingly, the given values have to be divided or multiplied accordingly for higher or lower concentration.

In a further preferred embodiment of the present invention, the pH value of the solutions has been optimized regarding physiologic acid-base-balance. Accordingly, it is in particular preferred that the pH values of the aqueous solutions are within the range of 4.8 to 6.5.

The use of at least 20% by weight of branched chain amino acids is in particular preferred. W. Hartig, Moderne Infusionstherapie, Parenterale Ernährung, VEB Johann Ambrosius Barth 1989, pages 451 to 455 describes a preferred selection of amino acids according to Rose. The table on page 451 relating to essential amino acids only indicates an amount of the branched chain amino acids isoleucine, leucine and valine in an amount of 40,9%. Corresponding to a preferred amino acid solution having a content of essential amino acids in an amount of 42%. This amount of branched chain amino acids corresponds to an amount of 17,2% by weight.

On the other hand, according to the present invention, a significant enlargement of the amount of branched chain amino acids was available in comparison to the above Rose pattern (approximately 18% by weight). This improvement leads to an approximation to the amino acid pattern of egg protein for which the complete bioavailability is assumed.

In this respect not only the amount of branched chain amino acids is of importance but the relation to the amount in relation other amino acids. In particular the branched chain amino acids dominate (in particular limit) the solubility of the amino acids as such due to the relative pure solubility thereof According to the knowledge of the inventors there is no other amino acid solution known or available which has an amino acid concentration of at least 15% by weight containing an amount of branched chain amino acids of 20% by weigh t based on the total amount of amino acids or more. Accordingly, the amount of branched amino acids is in particular of importance for amino acid solutions of the high preferable concentration such as 16 or 18% (by weight of amino acids).

It has also been considered that the potential base excess of the used am no acid solution does not exceed 20 mmol/day by using the maximum recommended dosage of amino acids 2 g protein/kg body weight and day.

By choosing the electrolyte composition (chloride, acetate, malate, citrate in the case of the electrolyte containing solutions) as well as by using the amino acid salts alone (lysine/lysine acetate but also the available aspartates, glutamates and pyro-glutamates) it had been considered that the potential base excess should be preferably between −10 and +10 mmol/l in the final product. For the electrolyte containing variations of the aqueous solution the potential base excess should be preferably close to 0 (+/−5 mmol/l). For the electrolyte-free variations of the solutions according to the present invention the possibility of the base excess adjustment is limited because the solutions have to be chloride-free and therefore, the potential base excess varies preferably in the range of −15 to −8 mmol/l in these solutions. The relatively negative base excess of the electrolyte-free variations of the solutions according to the present invention causes no problems, if in particular the electrolyte-free amino acid solution is part of the therapy conception.

Electrolyte-free amino acid solutions must be mixed with electrolyte solutions to balance the electrolyte intake of the patient during the administration. The compositions according to the present invention are in particular based on the experience in the field of known amino acid solutions which are in the market for many years. The specific pattern of the amino acids according to the present invention is the result of many years of clinical experiments with solutions available in the market, now with the new development taking into account the physiological aspect of the base excess, the galenic aspect of the formulations and the stability of the product in addition to the amino acid pattern. In view of the high solubility of the amino acids when following the above mentioned pattern a great variation of the amount of amino acid and electrolyte can be provided. Thus, the same base solution may be the basis of a 10% solution (corresponding to 100 g/l amino acids to correspond to other 3, 5, 8 or even 16 to 18% concentrations).

In case the aqueous solution according to the present invention contains amino acids and carbohydrates like glucose in one container, usually a reaction between these components take place depending mainly on the temperature and also on oxygen content of the mixture. The so-called Maillard-reaction causes a yellow color of the final product. This is in particular in the case of total parenteral solutions being in the market. These solutions are therefore produced aseptically without the usual heat sterilization at temperatures above 121° C.

The reaction between glucose and amino acids ends up with the formation of Maillard-products (yellow/brown colored condensation products), thus resulting in a concentration loss of some of the available amino acids in the solution. This phenomenon has been described extensively in the literature. It is important to know in this connection the influence of the physiological salts (phosphate, glycerophosphate, acetate, chloride, citrate, lactate and malate) on the reaction kinetic of the above-mentioned Maillard-reaction, influencing lately the stability of the solution and finally the shelflife of the medical preparation. This connection is not or only rarely investigated and published. The various solutions according to the present invention are optimized regarding the base excess as well as the kinetic of the above mentioned Maillard-reaction.

The base excess may be calculated as following:

Base excess $(BE)[v] = (TA + 24)$

TA: Titration acidity (mmol/l NaOH for reaching pH value 7.4)

24 mmol/l Na bicarbonate in blood

Potentional $BE$ $(Pot.BE) = (ME + BE)$

ME: Metabolic effect (metabolization of $R\text{—COOH} > CO_2$)

e.g.: $ME = $ (Acetate-Concentration) + (Lactate-Concentration) + 2(Malate-Concentration) + 3(Citrate-Concentration)

In a further preferred embodiment the aqueous solution according to the present invention are characterized in that the pattern of the amino acids calculated on the basis of 100 g/l of the amino acids is:

| | |
|---|---|
| Isoleucine | 4.7–5.3 g/l |
| Leucine | 8.5–9.5 g/l |
| Lysine | 6.5–7.5 g/l |
| Methionine | 4.0–5.0 g/l |
| Phenylalanine | 4.5–5.5 g/l |
| Threonine | 4.0–5.0 g/l |
| Tryptophane | 1.5–1.7 g/l |
| Valine | 6.0–7.0 g/l |
| Arginine | 11.0–12.0 g/l |
| Histidine | 2.5–3.5 g/l |
| Alanine | 10.0–11.0 g/l |
| Aminoacetic Acid (Glycine) | 11.0–12.0 g/l |
| Asparagine | 0–0.5 g/l |
| Aspartic Acid | 5.5–6.0 g/l |
| Acetylcysteine | 0.2–1.0 g/l** |
| Glutamic Acid | 6.0–8.0 g/l |
| Ornithine | 0–0.5 g/l |
| Proline | 5.0–6.0 g/l |
| Serine | 2.0–3.0 g/l |
| Tyrosine* | 0.3–0.5 g/l |
| *as Acetyltyrosine | 0–2.0 g/l |
| Taurine | 0–2.5 g/l |

**susceptible to oxidation, thus, dosage may depend on manufacturing technology and container as well In the same way a further embodiment of the present invention is characterized in that the pattern of electrolytes being:

| | |
|---|---|
| Sodium | 25, 0–75, 0 mmol/l |
| Potassium | 20, 0–30, 0 mmol/l |
| Magnesium | 20, 0–30, 0 mmol/l |
| Calcium | 0–4.0 mmol/l |
| Zinc | 0–0.04 mmol/l |
| Phosphate | 5.0–15.0 mmol/l |
| Chloride* | 25.0–75.0 mmol/l |
| Acetate* | 25.0–75.0 mmol/l |
| Citric acid | 1.0–3.0 mmol/l |
| Malate | 0–40.0 mmol/l |
| Lactate | 0–5.0 mmol/l |
| Glycerophosphate | 5–30.0 mmol/l and/or |
| Gluconate | 25–120.0 mmol/l |

The expression of the term "mammals" according to the present invention of course includes all kinds of mammals, in particular human beings.

Embodiment

| Amino Acid | 100 |
|---|---|
| % | [g/l] |
| Isoleucine | 5.00 |
| Leucine | 8.90 |
| Lysine | 6.81 |
| Methionine | 4.40 |
| Phenylalanine | 4.70 |
| Threonine | 4.20 |
| Tryptophane | 1.60 |
| Valine | 6.20 |
| Arginine | 11.50 |
| Histidine | 3.00 |
| Alanine | 10.50 |
| Aminoacetic Acid (Glycine) | 12.00 |
| Asparagine | |
| Aspartic Acid | 5.60 |
| Acetylcysteine | 0.21 |
| Glutamic Acid | 7.20 |
| Ornithine | |
| Proline | 5.50 |
| Serine | 2.30 |
| Tyrosine | 0.40 |

| Electrolytes | 10 [mol/l] |
|---|---|
| Sodium | 50.0 |
| Potassium | 25.0 |
| Magnesium | 2.5 |
| Calcium | — |
| Phosphate | 10.0 |
| Zinc | — |
| Chloride | 52.0 |
| Acetate | 46.0 |
| Citric acid | 2.0 |
| Malate | — |
| Lactate | — |
| Glycerophosphate | — |
| Gluconate | — |

The entire text of European Application Serial No.: 99 112 319.1 is incorporated herein by reference. All publications and patent applications mentioned in this specification are herein incorporated by reference to the same extent as if each individual publication or patent application was specifically and individually indicated to be incorporated by reference.

What is claimed is:

1. Aqueous solution of the parenteral nutrition of mammals consisting of:

a) a pattern of amino acids calculated on the basis of 100 g/l of amino acids:

| | |
|---|---|
| Isoleucine | 4.0–5.5 g/l |
| Leucine | 8.0–10.0 g/l |
| Lysine | 6.0–8.0 g/l |
| Methionine | 4.0–6.0 g/l |
| Phenylalanine | 4.0–6.0 g/l |
| Threonine | 4.0–6.0 g/l |
| Tryptophane | 1.0–2.0 g/l |
| Valine | 6.0–8.0 g/l |
| Arginine | 10.0–12.0 g/l |
| Histidine | 1.5–3.5 g/l |
| Alanine | 9.0–12.0 g/l |
| Aminoacetic Acid (Glycine) | 11.0–16.0 g/l |
| Asparagine | 0–1.0 g/l |
| Aspartic Acid | 5.5–8.0 g/l |
| Acetylcysteine | 0–2.5 g/l |
| Glutamic Acid | 6.0–10.0 g/l |
| Ornithine | 0–1.0 g/l |
| Proline | 4.0–6.0 g/l |
| Serine | 1.0–3.0 g/l |
| Tyrosine* | 01.–0.5 g/l |
| *as Acetyltyrosine | 0–2.0 g/l |
| Taurine | 0–4.0 g/l | b) a pattern of electrolytes of:

| | |
|---|---|
| Sodium | 0–100.0 mmol/l |
| Potassium | 0–80.0 mmol/l |
| Magnesium | 0–8.0 mmol/l |
| Calcium | 0–8.0 mmol/l and/or |
| Zinc | 0–0.08 mmol/l |
| Phosphate | 0–20.0 mmol/l |
| Chloride | 0–120.0 mmol/l |
| Acetate | 0–120.0 mmol/l |
| Citric acid | 0–10.0 mmol/l |
| Malate | 0–80.0 mmol/l |
| Lactate | 0–10.0 mmol/l |
| Glycerophosphate | 0–30.0 mmol/l and/or |
| Gluconate | 0–120.0 mmol/l | and c) optionally a carbohydrate solution and/or a fat emulsion.

2. Solution according to claim 1, characterized in that the content of amino acid varies in the range of 20 to 180 g/l.

3. Solution according to claim 1, characterized in that the pH value is in the range of 4.8 to 6.5.

4. Solution according to claim 1, characterized by an amount of 20% by weight of branched chain amino acids.

5. Solution according to claim 1, characterized by an amount of at least 42% by weight of essential amino acids.

6. Solution according to claim 1, characterized by an amount of at least 24% of precursors selected from Asp, Glu and/or Arg.

7. Solution according to claim 1, characterized in that the potential base excess is within the range of −10 to +10 mmol/l.

8. Solution according to claim 1, characterized in being sulfite-free.

9. Solution according to claim 1, characterized in that the pattern of the amino acids calculated on the basis of 100 g/l of amino acids is:

| | |
|---|---|
| Isoleucine | 4.7–5.3 g/l |
| Leucine | 8.5–9.5 g/l |
| Lysine | 6.5–7.5 g/l |
| Methionine | 4.0–5.0 g/l |
| Phenylalanine | 4.5–5.5 g/l |
| Threonine | 4.0–5.0 g/l |
| Tryptophane | 1.5–1.7 g/l |
| Valine | 6.0–7.0 g/l |
| Arginine | 11.0–12.0 g/l |
| Histidine | 2.5–3.5 g/l |
| Alanine | 10.0–11.0 g/l |
| Aminoacetic Acid (Glycine) | 11.0–12.0 g/l |
| Asparagine | 0–0.5 g/l |
| Aspartic Acid | 5.5–6.0 g/l |
| Acetylcysteine | 0.2–1.0 g/l |
| Glutamic Acid | 6.0–8.0 g/l |
| Ornithine | 0–0.5 g/l |
| Proline | 5.0–6.0 g/l |
| Serine | 2.0–3.0 g/l |
| Tyrosine* | 0.1–0.5 g/l |
| *as Acetyltyrosine | 0–2.0 g/l |
| Taurine | 0–2.5 g/l |

10. Solution according to claim 1, characterized in that the pattern of electrolytes being:

| | |
|---|---|
| Sodium | 25,0–75,0 mmol/ |
| Potassium | 20,0–30,0 mmol/l |
| Magnesium | 20,0–30,0 mmol/l |
| Calcium | 0–4.0 mmol/l and/or |
| Zinc | 0–0.04 mmol/l |
| Phosphate | 5.0–15.0 mmol/l |
| Chloride | 25.0–75.0 mmol/l |
| Acetate | 25.0–75.0 mmol/l |
| Citric acid | 1.0–3.0 mmol/l |
| Malate | 0–40.0 mmol/l |
| Lactate | 0–5.0 mmol/l |
| Glycerophosphate | 5–30.0 mmol/l and/or |
| Guconate | 25–120.0 mmol/l |

\* \* \* \* \*